(12) United States Patent
Griffiths et al.

(10) Patent No.: US 11,191,565 B2
(45) Date of Patent: Dec. 7, 2021

(54) SURGICAL ACCESS PORT AND ASSEMBLY

(71) Applicant: ALESI SURGICAL LIMITED, Cardiff (GB)

(72) Inventors: Dominic Griffiths, Cardiff (GB); Nicholas Evans, Cardiff (GB); Peter Bannister, Cardiff (GB); Neil Warren, Cardiff (GB); Francis Kweku Egyin Amoah, Cardiff (GB)

(73) Assignee: ALESI SURGICAL LIMITED, Cardiff (GB)

( * ) Notice: Subject to any disclaimer, the term of this patent is extended or adjusted under 35 U.S.C. 154(b) by 507 days.

(21) Appl. No.: 15/432,220

(22) Filed: Feb. 14, 2017

(65) Prior Publication Data
US 2017/0164977 A1  Jun. 15, 2017

Related U.S. Application Data

(63) Continuation of application No. PCT/GB2015/052369, filed on Aug. 14, 2015.

(30) Foreign Application Priority Data

Aug. 15, 2014  (GB) .................................... 1414533

(51) Int. Cl.
*A61B 17/34* (2006.01)
*B03C 3/38* (2006.01)

(52) U.S. Cl.
CPC ...... *A61B 17/3423* (2013.01); *A61B 17/3476* (2013.01); *B03C 3/38* (2013.01);
(Continued)

(58) Field of Classification Search
CPC ............ A61B 17/3423; A61B 17/3476; A61B 2017/3445; B03C 3/38
See application file for complete search history.

(56) References Cited

U.S. PATENT DOCUMENTS 4,959,063 A  9/1990 Kojima
5,183,471 A  2/1993 Wilk
(Continued)

FOREIGN PATENT DOCUMENTS

EP  0508453 A1  10/1992
GB  2495137 A  4/2013
(Continued)

*Primary Examiner* — Ariana Zimbouski
(74) *Attorney, Agent, or Firm* — Joseph C. Zucchero; Carolyn S. Elmore; Elmore Patent Law Group, P.C.

(57) ABSTRACT

A surgical access port and assembly are disclosed for providing access for a medical instrument into an intracorporeal cavity of a patient undergoing surgery. The access port comprises a cannula and a first passage which extends along the cannula and along which a medical instrument is arranged to pass, the passage comprising a first entrance portion disposed at a proximal region the of the cannula and a first exit portion disposed at a distal region of the cannula. The cannula further comprises a second passage which extends along the cannula and along which an electrode is arranged to pass, the second passage comprising a second entrance portion disposed at a proximal region of the cannula and a second exit portion disposed at a distal region of the cannula. The first exit portion of the first passage and the second exit portion of the second passage diverge along the cannula in a direction which is from the proximal end to the distal end of the cannula, to suitably locate the electrode with respect to a medical instrument.

17 Claims, 5 Drawing Sheets

(52) U.S. Cl.
CPC .............. *A61B 2017/3437* (2013.01); *A61B 2017/3445* (2013.01); *A61B 2218/008* (2013.01); *B03C 2201/26* (2013.01)

(56) References Cited

U.S. PATENT DOCUMENTS

| | | | |
|---|---|---|---|
| 5,383,860 A | | 1/1995 | Lau |
| 5,501,691 A | * | 3/1996 | Goldrath ............ A61B 17/0469 604/158 |
| 5,618,309 A | | 4/1997 | Green et al. |
| 5,810,776 A | | 9/1998 | Bacich et al. |
| 7,001,380 B2 | | 2/2006 | Goble |
| 8,597,301 B2 | | 12/2013 | Mitchell |
| 2005/0090819 A1 | | 4/2005 | Goble et al. |
| 2009/0105711 A1 | | 4/2009 | Mitchell |
| 2010/0094200 A1 | * | 4/2010 | Dean ...................... B01D 46/10 604/26 |
| 2012/0067212 A1 | * | 3/2012 | Warren ................. A61B 18/00 95/57 |
| 2012/0143134 A1 | * | 6/2012 | Hollis ................ A61B 17/3421 604/164.01 |
| 2014/0228836 A1 | | 8/2014 | Amoah et al. |
| 2014/0243593 A1 | * | 8/2014 | Goode ................ A61N 1/0509 600/104 |
| 2014/0316231 A1 | * | 10/2014 | Luhta ....................... A61B 5/25 600/394 |
| 2015/0182708 A1 | | 7/2015 | Barnard |

FOREIGN PATENT DOCUMENTS

| | | |
|---|---|---|
| JP | 3691672 B2 | 12/1998 |
| JP | H11342107 A | 12/1999 |
| JP | 2000507119 A5 | 11/2004 |
| JP | 2000175931 A | 6/2006 |
| JP | 2012533380 A | 12/2012 |
| RU | 2428945 C1 | 9/2011 |
| RU | 115635 U1 | 5/2012 |
| WO | 2011010148 A2 | 1/2011 |
| WO | 2013056121 A2 | 4/2013 |

* cited by examiner

SURGICAL ACCESS PORT AND ASSEMBLY

The present invention relates to a surgical access port and assembly for providing access for a medical instrument into an abdominal cavity of a patient undergoing intracorporeal surgery.

WO2011/010148 discloses apparatus for ionising gaseous, particulate-containing matter, such as smoke, disposed within an abdominal cavity of a patient undergoing a surgical procedure. The apparatus comprises the use of an electrode which is arranged to extend intracorporeally and a further electrode which is secured to the patient. The electrodes are connected to opposite poles of a high voltage (direct current) (DC) source and, for example, the electrode which extends into the abdominal cavity is negatively charged and arranged to emit a stream of electrons. The electrons and resulting gas ions that are created transiently attach themselves to the particulate-matter causing the matter to become attracted to the positively-charged patient tissue. In one application, surgical smoke can be cleared away from the site of a surgical procedure, to improve a surgeon's view of the surgical site.

The electrode which extends within the abdominal cavity must be located proximate to the surgical site to suitably charge the smoke particles which emanate therefrom during a surgical procedure. However, the electrode must not be positioned too close to the surgical site since there is a risk that the surgeon may contact the electrode with a surgical instrument. Any direct contact of a surgical instrument with the electrode will result in a direct electrical short through the patient which compromises performance and also introduces the risk of an accidental, non-harmful static discharge to the operator.

We have now devised an improved surgical access port and surgical access port assembly which facilitates a suitable positioning of the electrode.

In accordance with the present invention, there is provided a surgical access port for providing access for a medical instrument into an intracorporeal cavity of a patient undergoing surgery, the access port comprising:
 a cannula;
 a first passage which extends along the cannula and along which a medical instrument is arranged to pass, the passage comprising a first entrance portion disposed at a proximal region of the cannula and a first exit portion disposed at a distal region of the cannula;
 a second passage which extends along the cannula and along which an electrode is arranged to pass, the second passage comprising a second entrance portion disposed at a proximal region of the cannula and a second exit portion disposed at a distal region of the cannula;
 wherein the first exit portion of the first passage and the second exit portion of the second passage diverge along the cannula in a direction which is from the proximal end to the distal end of the cannula.

Advantageously, the redirection of the second exit portion of the second passage, away from the first passage serves to direct an electrode away from the cannula and thus any medical instruments which may be located within the first passage. This separation of the electrode from the medical instrument for example, preserves a suitable potential difference between the electrode and the patient for ionising particulates suspended in the intracorporeal cavity.

In an embodiment, the second exit portion preferably comprises an arcuate portion.

In an embodiment, the first and second exit portions terminate at a first and second exit port, respectively. The first exit port is preferably disposed at a distal end of the cannula. In an embodiment, the second exit port is spaced from the first exit port, longitudinally of the cannula, and is preferably disposed in a side wall of the cannula.

In an embodiment, the surgical access port further comprises a head having an access passage which extends there through, between a proximal and distal end of the head, for receiving a surgical instrument. The cannula preferably extends from the distal end of the head and at least the entrance portion of the first passage is aligned with the access passage. Preferably, the first passage comprises a substantially linear passage, such that the first entrance portion and first exit portion are substantially collinear.

In an embodiment, the head further comprises a receiver passage which extends through the head, for receiving an electrode. The receiver passage preferably comprises a receiver exit portion which is aligned with the second entrance portion of the second passage, so that an electrode can pass into the second passage via the receiver passage. In an alternative embodiment, the surgical access port comprises an electrode receiver housing having a receiver passage which extends there through. The receiver passage preferably comprises a receiver exit portion which is aligned with the second entrance portion.

In an embodiment, the receiver passage comprises a substantially linear passage.

The surgical access port may further comprise a sharpened distal end of the cannula for penetrating an abdominal wall of a patient.

According to a second aspect of the present invention, there is provided a surgical access port assembly for providing access for a medical instrument into an intracorporeal cavity of a patient undergoing surgery, the access port assembly comprising the surgical access port of the first aspect and an electrode for removable insertion within the second passage of the cannula.

In an embodiment, the electrode comprises an ion emission zone disposed at distal region thereof, which is arranged to extend out from the second exit port. The ion emission zone may comprise a fibrous emission zone or alternatively, a sharpened distal end of the electrode. In use, the ion emission zone is preferably spaced from the cannula by a distance in the range of 5-50 mm and more preferably 10-30 mm.

In an embodiment, the access port assembly further comprises an electrically conductive conduit which is arranged to couple with the medical instrument and with a patient undergoing the surgery. In an embodiment, the conduit may comprise an electrically conductive portion of the port, which is arranged to form an electrical coupling with the patient when inserted through tissue layers of the patient, such as an abdominal wall. In an alternative embodiment, the conduit may comprise a strap. The strap may comprise first means, such as a clip, disposed at one end thereof for electrically coupling the strap to the medical instrument, and second means, such as an adhesive pad, disposed at the other end for electrically coupling the strap to the patient. The conductive conduit provides a conductive path for any charge which accumulates on the medical instrument, to return to the electrode positioned on the patient.

In an embodiment, the assembly further comprises a high voltage, direct current (DC) electrical source which is electrically connectable to the electrode for generating ions from a distal end of the electrode within the abdominal cavity.

Embodiments of the present invention will now be described by way of example only and with reference to the accompanying drawings, in which.

Figure 1:
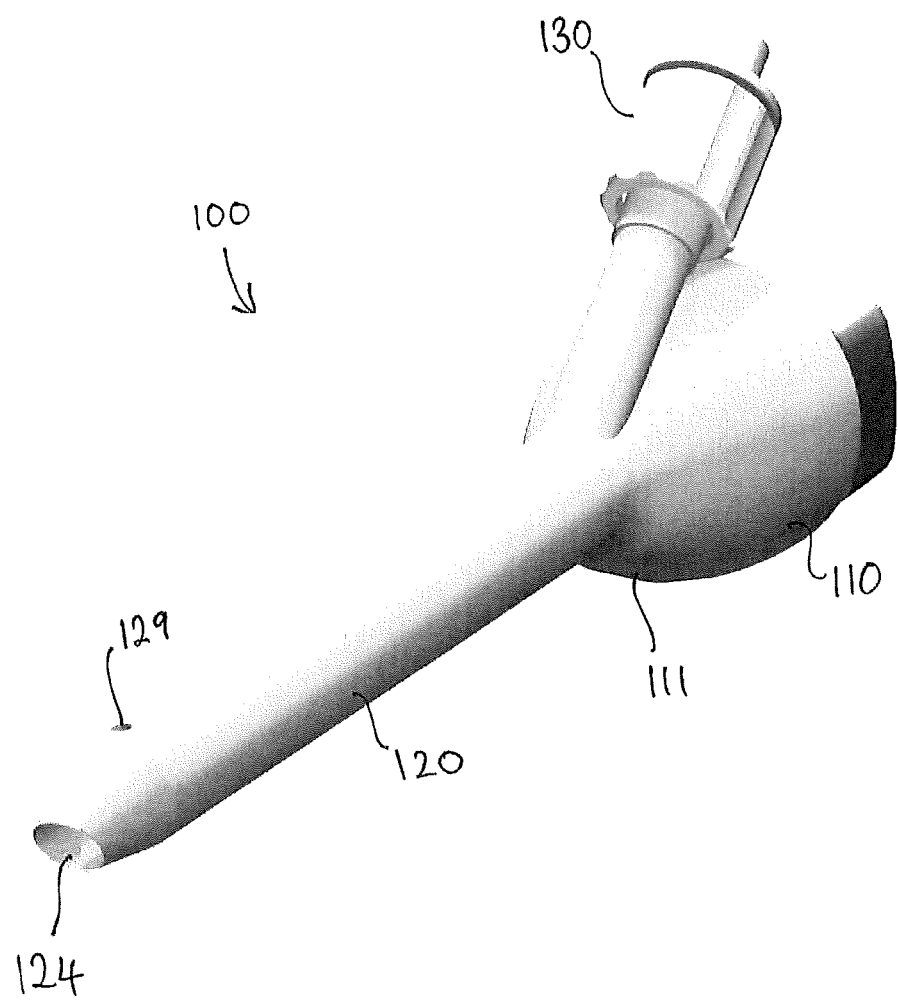
FIG. 1 is a perspective view of a surgical access port according to a first embodiment of the present invention.
Figure 3A:
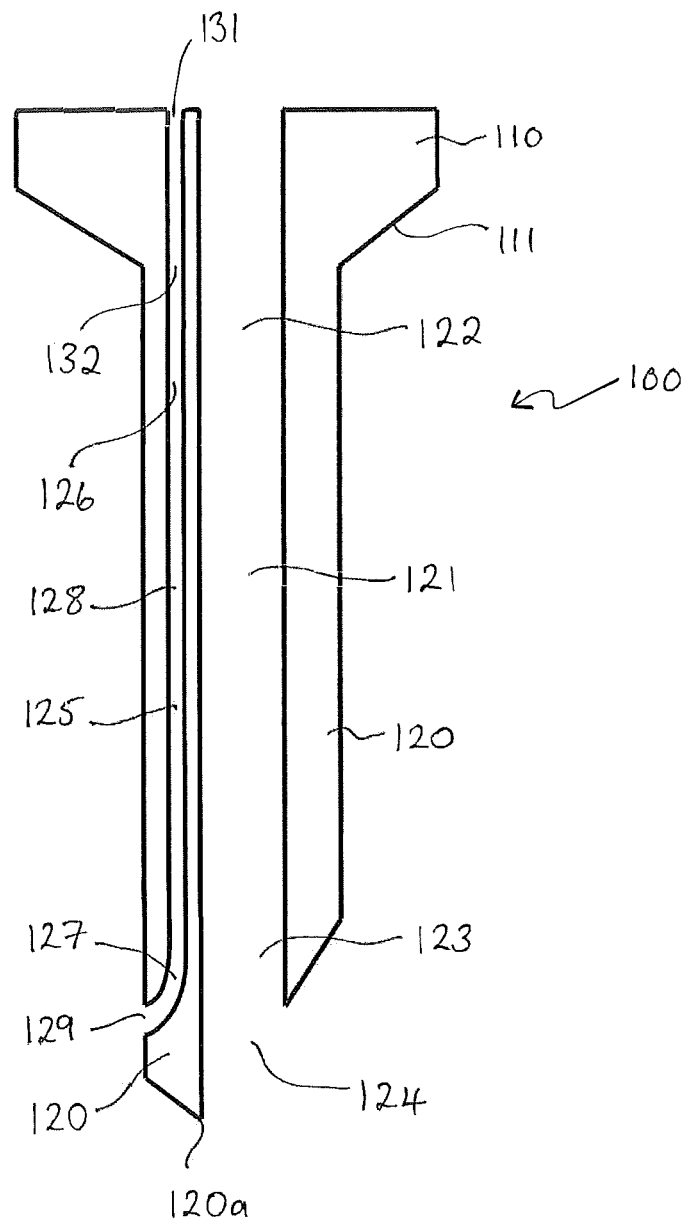
FIG. 3a is a sectional view along a surgical access port according to a second embodiment of the present invention.
Figure 3B:
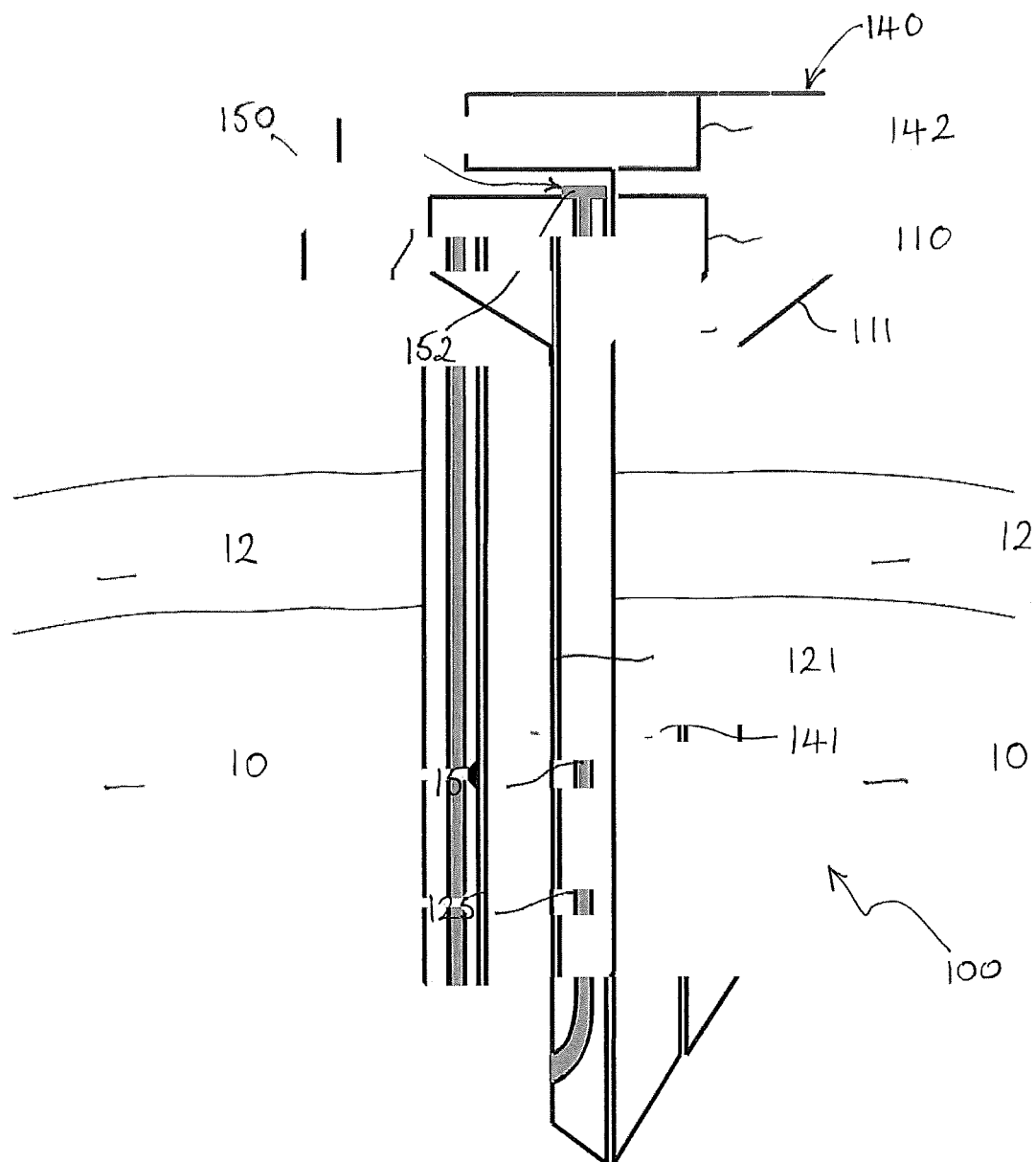
FIG. 3b is a sectional view along the surgical access port illustrated in FIG. 3a located within an abdominal wall of a patient.
Figure 4:
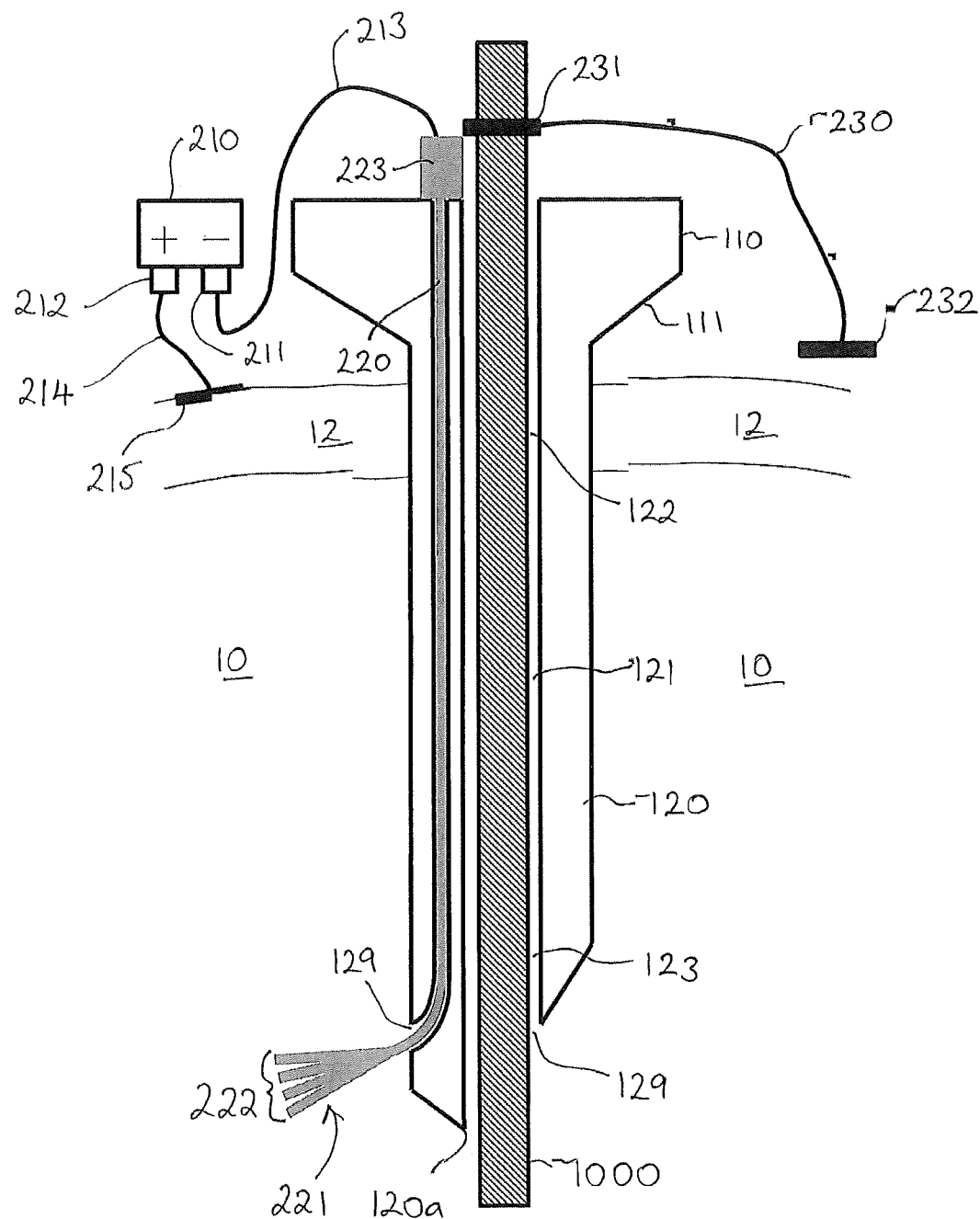
FIG. 4 is a sectional view along a surgical access port assembly according to an embodiment of the present invention, with the surgical access port located within an abdominal wall of a patient.

Referring to FIG. 1 of the drawings, there is illustrated a perspective view of a surgical access port 100 according to a first embodiment of the present invention, for providing intracorporeal access for a medical instrument 1000 (illustrated in FIG. 4 of the drawings) into a cavity, such as an abdominal cavity 10 (as illustrated in FIGS. 3b and 4 of the drawings) through tissue layers, such as an abdominal wall 12 of a patient (not shown) during surgery. The access port 100 comprises a head 110 having a generally circular cross-sectional shape and an elongate cannula 120, integrally formed therewith, having a generally circular cross-section along the length thereof. The head 110 comprises a larger diameter than the cannula 120 and the interface between the head 110 and the cannula 120 is defined by a head taper 111 portion, along which the cross-sectional area decreases from that of the head 110 to that of the cannula 120. In use, the head taper 111 is arranged to rest upon an external tissue area 12 of the patient (not shown) to prevent the access port 100 from passing completely into the abdominal cavity 10.

Figure 2:
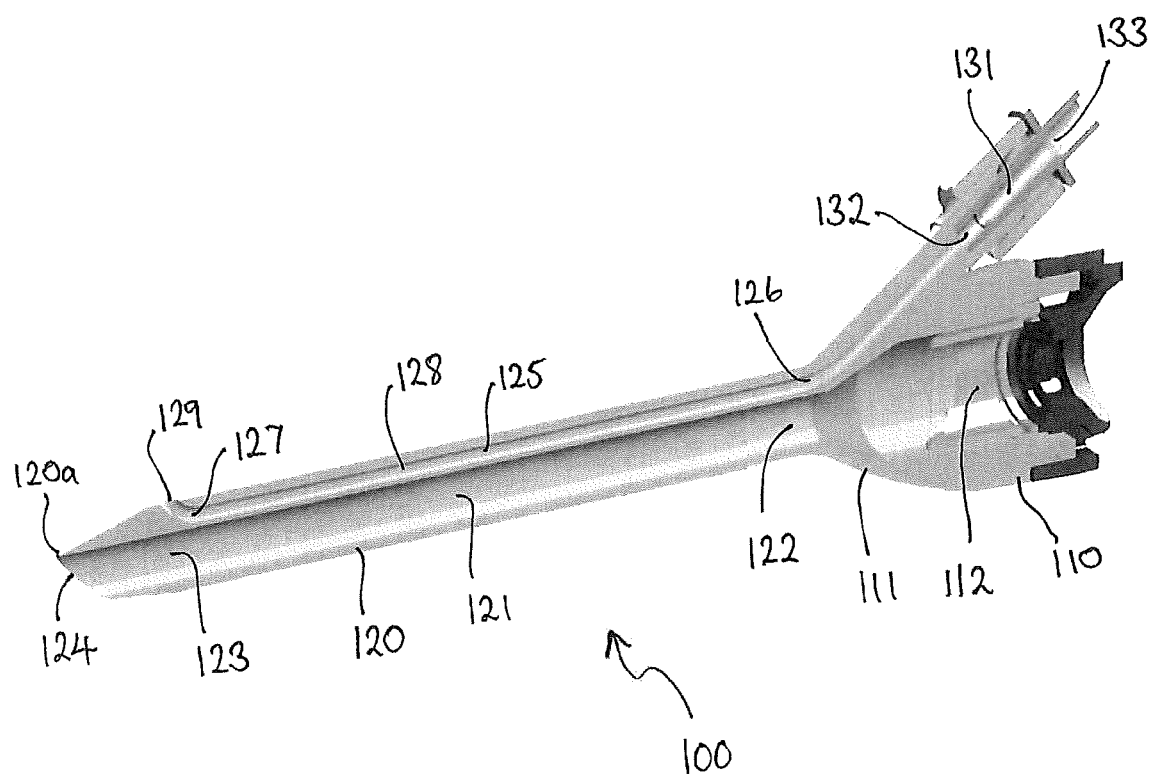
FIG. 2 is a sectional view along the surgical access port illustrated in FIG. 1.

Referring to FIG. 2 of the drawings, the head 110 and head taper 111 comprise an access passage 112 which extends therethrough and which is aligned with an entrance portion 122 of a first passage 121 which extends through the cannula 120. The entrance portion 122 is aligned with the access passage 112 and is orientated substantially coaxially with the access passage 112, such that the transition from the access passage 112 to the first passage 121 comprises a continuous, smooth transition. The first passage 121 extends from a proximal end of the cannula 120 to a distal end of the cannula 120 and a distal region of the first passage 121 is defined by an exit portion 123 which terminates at an exit port 124 disposed at a distal end of the cannula 120. In an embodiment, the access passage 112 and the first passage 121 are substantially linear passages which are orientated coaxially and are arranged to receive surgical instruments 1000 so that a surgeon can easily pass the instruments 1000 through a patients' abdominal wall 12 into the abdominal cavity 10.

The surgical access port 100 further comprises a second passage 125 which extends along the cannula 120. The second passage 125 comprises an entrance and exit portion 126, 127 disposed at opposite ends of the second passage 125. In a first embodiment, as illustrated in FIGS. 1 and 2 of the drawings, the entrance portion 126 comprises an arcuate portion of the second passage 125, such that the entrance portion 126 converges toward the first passage 121 in a direction which is along the cannula 120 from the proximal end to the distal end thereof. The entrance portion 126 of the second passage 125 is aligned with an exit portion 132 of a receiver passage 131 disposed within an electrode receiver housing 130 which extends adjacent the head 110. The receiver housing 130 extends to one side of the head 110 and comprises an entrance port 133 for enabling a surgeon (not shown) to pass an electrode 220 into the second passage 125 via the receiver passage 131. In this respect, the exit portion 132 of the receiver passage 131 and entrance portion 126 of the second passage 125 are aligned to provide for a continuous, smooth transition there between.

In a second embodiment, as illustrated in FIG. 3a of the drawings, the receiver housing 130 is formed as part of the head 110 and the receiver passage 131 extends through the head 110 in a substantially parallel orientation with the access passage 112. The exit portion 132 of the receiver passage 131 and the entrance portion 126 of the second passage 125 are thus substantially linear passages.

The second passage 125 of the first and second embodiments further comprises an intermediate portion 128 which extends between the entrance and exit portions 126, 127 thereof. The intermediate portion 128 comprises a substantially linear portion which extends substantially parallel with the first passage 121. The exit portion 127 of the second passage 125 of the first and second embodiments comprises an arcuate section which diverges from the first passage 121 in a direction which is from the proximal to the distal end of the cannula 120. The second passage 125 terminates at an exit port 129 disposed in a side wall of the cannula 120 and is thus spaced from the exit port 124, longitudinally of the cannula 120.

Referring to FIG. 3b of the drawings, the access port 100 further comprise a trocar 140 and obturator 150, which are arranged to respectively close the first and second passages 121, 125. The trocar 140 and obturator 150 are shown in relation to the access port 100 of the second embodiment, however, the trocar 140 and obturator 150 may be also provided with the access port 100 of the first embodiment. The trocar 140 comprises a elongate rod 141 or similar which is extends from a cap region 142. The rod 141 is sized to extend within and substantially match the length of the first passage 121, to seal the passage 121 and minimise any ingress of bodily fluid and/or tissue as the port 100 is inserted through tissue layers, such as an abdominal wall 12 of a patient. The distal end of the rod 141 may be sharpened to facilitate the insertion of the access port 100 through the tissue layers. Similarly, the obturator 150 comprises an elongate filament 151, which is arranged to seal the second passage 125. The filament 151 extends from a bung 152 which is arranged to abut a proximal side of the head 110 and the filament 151 is sized such that the length substantially matches the length of the second passage 125.

Referring to FIG. 4 of the drawings, there is illustrated a surgical access port assembly 200 according to an embodiment of the present invention for providing access for a medical instrument 1000 into an abdominal cavity 10 of a patient undergoing surgery. The assembly 200 comprises the surgical access port 100 of the second embodiment, however, it is to be realised that the assembly 200 may be realised using the surgical access port 100 of the first embodiment, as illustrated in FIGS. 1 and 2 of the drawings.

The surgical access port assembly 200 further comprises a high voltage, direct current (DC) electrical source 210 and an electrode 220, which is arranged to pass along the second passage 125 of the surgical access port 100. The electrode 220 is substantially linear and comprises an ion emission zone 221 disposed at a distal region thereof for generating ions within the abdominal cavity 10 of a patient (not shown). The ion emission zone 221 may comprise a sharpened distal end of the electrode or in an alternative embodiment, the ion emission zone may comprise a plurality of electrode fibres 222. The electrode 220 further comprises a head 223 disposed at a proximal end thereof, which is arranged to abut the receiver housing 130, or head 110, to limit the extent that the electrode 220 can be inserted within the second passage 125. The electrode head 223 is further arranged to house circuitry (not shown) which acts as an interface between the electrode 220 and a wire 213 (see FIG. 4) or similar which delivers electrical current to the electrode 220 from the electrical source 210. It is found that alternating high voltages in neighbouring wires and conduits (not shown) can transfer an alternating voltage to the wire 213 delivering electrical energy to the electrode 220, via capacitive coupling. For example, medical monopolar diathermy instruments (not shown) which pass through the first passage 121 of the port 100 will have a wire or conduit (not shown) for delivering electrical power thereto. The wire or conduit will be subject to alternating high voltages to deliver the required electrical power to the instrument for performing the required cauterising and cutting of tissue. The wire (not shown) for the diathermy instrument will typically extend in close proximity to the wire 213. However, these alternating high voltages can transfer an apportionment of the voltage to the wire 213, which can result in the delivery of an electrical current to the patient via the electrode fibres 222. This can result in the electrode 220 potentially acting as a diathermy device itself. Accordingly, the electrical circuitry (not shown) disposed in the electrode head 223 comprises a resistive arrangement (not shown) for limiting the induced current flow to the electrode 220 from the wire 213 to prevent a potentially dangerous build up of electrostatic charge on the electrode.

The assembly 200 further comprises a conductive conduit 230 which is arranged in use, to electrically couple a medical instrument 1000 with the patient. In an embodiment, the conductive conduit may comprise one or more electrically conductive portions (not shown) disposed on the cannula 120 or head 110 of the port 100, which are arranged to electrically couple with the patient when inserted through tissue layers of the patient, such as an abdominal wall 12, and the medical instrument 1000. In an alternative embodiment, as illustrated in FIG. 4 of the drawings, the conductive conduit 230 may be provided by an electrically conductive strap having a clip 231 or similar at one end thereof for forming an electrical contact with the medical instrument 1000 and a contact pad 232, for suitably electrically coupling the strap 230, and thus the instrument 1000, with the patient, for example.

Referring to the embodiment of the assembly 200 illustrated in FIG. 4 of the drawings, in use, the trocar 140 is first inserted within the first passage 121 until the cap 142 abuts the proximal end of the head 110 and the obturator 150 is fully inserted within the second passage 125 to respectively seal the first and second passages 121, 125. The distal end of the access port 100 is then suitably positioned upon the abdominal wall 12 of the patient undergoing the surgery and pressure is applied to the cap 142 and thus the access port 100 to cause the distal end of the cannula 120 and rod 141 of the trocar 140 to penetrate the wall 12. In this respect, it is envisaged that the distal end of the cannula 120, in addition to the rod 141 of the trocar 140, may be sharpened or comprise an apex 120a or similar to facilitate wall penetration. The access port 100 is then further inserted into the abdominal cavity 10 until the required depth is achieved, and the trocar 140 and obturator 150 are removed. Once fully inserted, the head taper 111 may abut the outer side of the wall 12 to prevent the cannula from falling into the patient.

The distal end of the electrode 220, namely the ion emission zone 221 may then be inserted into the second passage 125 via the receiver passage 131. The electrode 220 is inserted until the detent 223 abuts the receiver housing 130 or head 110. The electrode is sized, so that once fully inserted, the ion emission zone 221 extends beyond the exit portion 127 of the second passage 125, outwardly of the cannula 120 from the exit port 129. The arcuate form of the exit portion 127 of the second passage 125 ensures that the electrode is directed away from the cannula 120, substantially transverse to a longitudinal axis of the first passage 121 and so that ion emission zone 214 becomes spaced from the wall of the cannula 120 by 5-50 mm and more preferably 10-30 mm.

The electrode 220 is then electrically coupled to one terminal 211 of the electrical source 210 via a wire 213 or similar, while the further terminal 212 is electrically coupled to the patient by coupling an electrical wire 214 between the further terminal 212 and an adhesive pad 215 which is bonded to the patient. The electrical potential difference between the electrode 220 and the patient tissue causes a stream of electrons and negative gas ions to emanate from the ion emission zone 221 of the electrode 220 and pass toward the positively charged internal tissue layer 12 of the patient.

A medical instrument 1000, such as cutting instrument or laparoscope (not shown) is then inserted into the intracorporeal cavity 10 of the patient via the access passage 112 in the head 110 of the port 100 and first passage 121 in the cannula 120 of the port 100. As the surgeon performs the surgical procedure, any smoke or airborne particles which develop will become ionised by the stream of electrons and negative gas ions, and become attracted toward the positively charged abdominal wall 12. The positioning of the electrode 220 minimises the possibility of any accidental contact with the surgical instrument 1000 and also reduces the extent to which the surgical instrument becomes electrically charged by the electrode. Furthermore, the position of the electrode 220 relative to the cannula and instrument therein minimises any reduction in output voltage that would otherwise be caused by a decrease in the resistance between the electrode and the cannula (or surgical instrument) were the two to be closely positioned, and which thus would reduce the ionisation of particles within the abdominal cavity 10.

As a safety measure, the instrument 1000 may be electrically coupled with the patient or the further terminal of the electrical source 210 via the conductive conduit 230, to provide an electrical path from the instrument 1000 to the electrical source 210. In the event that the surgical instrument 1000 accidentally contacts the electrode 220 and principally the ion emission zone 221, then the conductive conduit 230 can provide a short circuit return path to the electrical source, thereby bypassing the surgeon. In principle, additional conductive conduits could be applied to other surgical instruments similarly co-located intracorporeally during the procedure.

From the foregoing therefore it is evident that the surgical access port and assembly provides a simple yet effective means of suitably co-locating an electrode for ionising airborne particles in such a way that the performance of the electrode remains unaffected by the presence of electrostatically conductive materials, such as surgical instruments, whilst simultaneously mitigating the risk of electrostatic shock from such surgical instruments during surgical procedures Whilst the invention has been described above, it extends to any inventive combination of features set out above. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention claimed is:

1. A surgical access port assembly for providing access for a medical instrument into an intracorporeal cavity of a patient undergoing surgery, the access port assembly comprising:
    a cannula;
    a first passage which extends along the cannula and along which a medical instrument is arranged to pass, the passage comprising a first entrance portion disposed at a proximal region the of the cannula and a first exit portion disposed at a distal region of the cannula;
    an electrode;
    an electrode receiver housing having a receiver passage which extends therethrough, wherein the electrode receiver housing is in communication with the second passage;
    a second passage which extends along the cannula and along which the electrode is arranged to pass, the second passage comprising a second entrance portion disposed at a proximal region of the cannula and a second exit portion disposed at a distal region of the cannula;
    wherein the second entrance portion of the second passage converges toward the first passage in a direction which is from the proximal end to the distal end of the cannula, and
    wherein the first exit portion of the first passage and the second exit portion of the second passage diverge along the cannula in a direction which is from the proximal end to the distal end of the cannula;
    wherein the electrode comprises an ion emission zone disposed at the distal region thereof, which in use, is arranged to extend out from the second exit port and a head disposed at a proximal end thereof, which is arranged to abut the receiver housing, the electrode head further comprising an electrically resistive arrangement for limiting the induced current flow to the electrode; and,
    wherein the ion emission zone is spaced from the cannula by a distance of up to 50 mm to minimize the reduction in output voltage caused by a decrease in the resistance between the electrode and the cannula.

2. A surgical access port assembly according to claim 1, wherein the second exit portion comprises an arcuate portion.

3. A surgical access port assembly according to claim 1, wherein the first and second exit portions terminate at a first and second exit port, respectively.

4. A surgical access port assembly according to claim 3, wherein the first exit port is disposed at a distal end of the cannula.

5. A surgical access port assembly according to claim 3, wherein the second exit port is spaced from the first exit port, longitudinally of the cannula.

6. A surgical access port assembly according to claim 3, wherein the second exit port is disposed in a side wall of the cannula.

7. A surgical access port assembly according to claim 1, wherein the first passage comprises a linear passage, such that the first entrance and first exit portions are collinear.

8. A surgical access port assembly according to claim 1, further comprising a head having an access passage which extends therethrough, between a proximal and distal end of the head, for receiving a surgical instrument.

9. A surgical access port assembly according to claim 8, wherein the cannula extends from the distal end of the head and at least the entrance portion of the first passage is aligned with the access passage.

10. A surgical access port assembly according to any of claim 8, wherein the head further comprises a receiver passage which extends through the head, for receiving the electrode.

11. A surgical access port assembly according to claim 10, wherein the receiver passage comprises a receiver exit portion which is aligned with the second entrance portion of the second passage, so that the electrode can pass into the second passage via the receiver passage.

12. A surgical access port assembly according to claim 1, wherein the receiver passage comprises a receiver exit portion which is aligned with the second entrance portion.

13. A surgical access port assembly according to claim 10, wherein the receiver passage comprises a linear passage.

14. A surgical access port assembly according to claim 1, wherein the cannula comprises a sharpened distal end.

15. A surgical access port assembly according to claim 1, wherein the ion emission zone comprises a fibrous emission zone or a sharpened distal end of the electrode.

16. A surgical access port assembly according to claim 1, further comprising a high voltage, direct current (DC) electrical source which is electrically connectable to the electrode for generating ions from a distal end of the electrode within an abdominal cavity.

17. A surgical access port assembly according to claim 16, further comprising an electrically conductive conduit which is arranged to electrically couple with the medical instrument and with the electrical source, or a patient undergoing the surgery.

* * * * *